United States Patent
Weiss et al.

(10) Patent No.: US 7,175,784 B2
(45) Date of Patent: Feb. 13, 2007

(54) METHOD FOR THE PRODUCTION OF ALKYL LITHIUM COMPOUNDS BY USING REDUCED PRESSURE

(75) Inventors: Wilfried Weiss, Eschershauser (DE); Eike Dolling, Goslar (DE); Bernd Schneider, Bad Harzburg (DE)

(73) Assignee: Chemetall GmbH, Frankfurt am Main (DE)

( * ) Notice: Subject to any disclaimer, the term of this patent is extended or adjusted under 35 U.S.C. 154(b) by 357 days.

(21) Appl. No.: 10/498,186

(22) PCT Filed: Dec. 10, 2002

(86) PCT No.: PCT/EP02/13975

§ 371 (c)(1), (2), (4) Date: Aug. 20, 2004

(87) PCT Pub. No.: WO03/051891

PCT Pub. Date: Jun. 26, 2003

(65) Prior Publication Data

US 2005/0051911 A1   Mar. 10, 2005

(30) Foreign Application Priority Data

Dec. 18, 2001  (DE) ................. 101 62 332

(51) Int. Cl.
*C07F 1/02* (2006.01)
(52) U.S. Cl. .................................. 260/665 R
(58) Field of Classification Search ............. 260/665 R
See application file for complete search history.

(56) References Cited

U.S. PATENT DOCUMENTS

| 3,122,592 A | | 2/1964 | Eberly |
| 3,452,112 A | | 6/1969 | Morrison et al. |
| 5,211,887 A | | 5/1993 | Morrison et al. |
| 5,332,533 A | * | 7/1994 | Schwindeman et al. 260/665 R |
| 5,523,447 A | * | 6/1996 | Kamienski et al. ......... 556/466 |

FOREIGN PATENT DOCUMENTS

| WO | WO-95 01982 A | 1/1995 |
| WO | WO-96 40692 A | 12/1996 |

* cited by examiner

*Primary Examiner*—Thurman K. Page
*Assistant Examiner*—Yevgeny Valenrod
(74) *Attorney, Agent, or Firm*—Fulbright & Jaworski L.L.P.

(57) ABSTRACT

Disclosed is a method for producing Alkyllithium compounds by reacting metallic lithium with an Alkyl halide in a solvent. The reaction is performed at a reduced pressure at the boiling point of the solvent.

21 Claims, No Drawings

METHOD FOR THE PRODUCTION OF ALKYL LITHIUM COMPOUNDS BY USING REDUCED PRESSURE

The invention concerns a process for the production of alkyl lithium compounds under reduced pressure.

Alkyl lithium compounds are produced by reacting organic halogen compounds with metallic lithium. The reaction is conventionally performed in hydrocarbons or in ethers as solvent.

WO 95/01982 provides a detailed description of the production of alkyl lithium compounds from lithium metal dispersion and alkyl halide, mentioning the sodium content of the lithium, the lithium excess relative to the alkyl halide, the alkyl halide, the metering rate, the solvent, the influence of the traces of water in the reaction and the reaction temperature. Depending on the solvent used, the reaction between lithium and alkyl halide is performed at the boiling point of the solvent between 50 and 100° C., or between 50 and 125° C. below the boiling point of the solvent.

WO 96/40692 describes a process for the production of lithium-organic solutions, wherein cast or extruded lithium rods react with an alkyl halide (e.g. n-, s-, or t-butyl chloride) in a molar excess of 3:1 to 20:1 in a solvent under a protective gas atmosphere for 1 to 10 hours with moderate stirring, and the product is separated from lithium metal and the secondary product LiCl in the reactor. In a variant of the process likewise described in WO 96/40692, stirring is not performed during the reaction (the LiCl formed remains on the Li metal), the product solution is separated off, and after separating off the LiCl (e.g. by adding solvent, stirring and separating off the LiCl suspension) the excess Li metal together with newly added metal is reacted again with added alkyl halide in the replenished solvent.

The reaction of lithium with an alkyl halide is a highly exothermic reaction. The lithium is generally placed in the solvent and the alkyl halide metered in at the rate at which the reaction heat can be dissipated. In the production of n-butyl lithium in hexane, for example, the temperature increases rapidly from room temperature (20° C.) to the boiling point of hexane (68° C.). The reaction heat that is released can be dissipated through the reactor jacket or by evaporative cooling of the solvent (utilising the enthalpy of vaporisation of the solvent).

To achieve as rapid and complete a reaction as possible, an elevated temperature can in principle be chosen for the reaction of Li metal with alkyl halides, particularly alkyl chlorides, e.g. the boiling temperature of common solvents such as hexane (68° C.) or heptane (98° C.). Unfortunately this is not always practical, however, since an elevated temperature has a negative effect on the yield. Thus at elevated temperatures there is an increased occurrence of undesirable Wurtz reactions, thermal degradation of the alkyl lithium compounds and other secondary reactions. In the case of butyl lithium compounds, s-butyl lithium displays greater thermal sensitivity than n-butyl lithium. Isobutyl lithium displays especially high thermal sensitivity. In the case of n-alkyl lithium compounds, the aforementioned undesirable reactions occur in particular with synthesis in higher-boiling solvents than hexane such as heptane (a preferred solvent for alkyl lithium compounds) or octane. In the case of branched s- and t-alkyl lithium compounds this can be observed even at temperatures below the boiling point of hexane (68° C.). For these reasons t-butyl lithium, for example, is generally produced in boiling pentane at a temperature of only 33° C. If on the other hand the synthesis of alkyl lithium compounds is performed below the solvent boiling point, the scale of the undesirable secondary reactions is smaller because of the lower temperature, but the reaction is often retarded and accumulation of the alkyl halide can easily occur as a consequence, which in turn can allow the reaction to go out of control.

The object of the invention is to overcome the disadvantages of the prior art and to provide a process for the production of alkyl lithium compounds that allows as high as possible a reaction rate with high yields, without the occurrence of undesirable secondary reactions.

The object is achieved by a process in which metallic lithium is reacted with an alkyl halide in a solvent, wherein the reaction is performed under reduced pressure and at the boiling point of the solvent. "Reduced pressure" should be understood to mean that the pressure in the reaction vessel is below the ambient pressure (atmospheric pressure).

Although in this mode of reaction the reaction temperatures are below the boiling points under normal pressure of the solvents used, the particularly preferred reaction temperatures being 25 to 50° C., for example, the yield when the process is performed at reduced pressure is significantly higher than in a comparable reaction that is performed at the same temperature but under normal pressure. The reason for this may be that the boiling solvent forms vapour bubbles on the surface of the lithium, which make it easier for the LiCl that is formed to be detached from the Li metal surface.

Depending on the chosen solvent, the reaction is preferably performed under a pressure of 10 to 900 mbar, particularly preferably 50 to 500 mbar. Preferred temperatures are 0 to 80° C., particularly preferred temperatures 20 to 50° C.

An advantage of the process according to the invention is that when lithium is reacted with an alkyl halide in a solvent, a high and uniform reaction rate is achieved and at the same time secondary reactions are effectively suppressed because of the relatively low temperature. This applies in particular for more thermolabile alkyl lithium compounds, e.g. sec- and tert-butyl lithium and especially also isobutyl lithium. In addition, with the aid of the process according to the invention the reaction can be performed in higher-boiling solvents (e.g. cyclopentane, cyclohexane, methyl cyclohexane, heptane, octane, nonane, decane, toluene, ethyl benzene or mesitylene). Thus solutions of alkyl lithium compounds can be prepared in higher-boiling solvents without the need for a solvent exchange, as was previously the case. Another advantage is that the previously common use of ethers as solvent or solvent component (ethers serve to release Li halides from the Li surface) can be avoided. A further advantage of the process according to the invention is that butyl lithium can be synthesised in aromatic hydrocarbons such as toluene, for example, without this resulting in a metallisation of the aromatics.

As the reaction is performed according to the invention at the boiling point of the particular solvent, the reaction heat formed can advantageously be dissipated through the enthalpy of vaporisation of the solvent, which represents an advantage over the jacket cooling that is otherwise performed in reactions below the solvent boiling point.

The invention is described in more detail below by reference to examples.

EXAMPLE 1

Production of S-butyl Lithium in Cyclohexane at 40° C. under Vacuum 24.5 g of Li powder (3.60 mol) were stirred with 0.5 g of LiH powder in 100 ml of cyclohexane for 30 minutes at room temperature and the reaction initiated by the addition of 2 ml of s-butyl chloride.

A further 570 ml of cyclohexane (in total 500 g=670 ml) were added and the reaction was again initiated with 5 ml of s-butyl chloride. Following a temperature rise (reaction kick-off) the internal temperature was adjusted to 40° C. and the pressure reduced until the solvent came to the boil (250 mbar). The remaining s-butyl chloride (total amount 138 g, 1.49 mol) was then added within 80 minutes and the reaction continued for a further 60 minutes. The vacuum was then released with argon, the reaction mixture cooled to room temperature and filtered, and washed with cyclohexane.

663 g of a clear, almost colourless solution were obtained with 2.24 mmol of s-butyl lithium per g of solution.

Total amount of s-butyl lithium=1.49 mol (>99% yield).

COMPARATIVE EXAMPLE A

Production of S-butyl Lithium in Cyclohexane at 81° C. under Normal Pressure

In analogy to example 1, 10.0 g of Li powder (1.44 mol) were reacted in 253 g of cyclohexane with 40 g of s-butyl chloride within 1 hour, the reaction being performed in contrast to example 1 under normal pressure and the solvent boiling at 81° C. The reaction was continued for a further 30 minutes. The reaction solution obtained had a total base content of 1.31 mmol per g of solution, which corresponds to a yield of a maximum of 84.7%.

A comparison of the results from example 1 and comparative example A shows that the yield from the performance of the process according to the invention (reaction at reduced temperature but at boiling point due to the vacuum) is significantly higher than that from the performance of the known process (reaction at elevated temperature at boiling point under normal pressure).

EXAMPLE 2

Production of T-butyl Lithium in Hexane at Various Temperatures under Vacuum 21.0 g of Li powder (3.02 mol) were stirred with 0.1 g of LiH powder in 100 ml of hexane for 30 minutes at room temperature and the reaction initiated by addition of 2 ml of t-butyl chloride.

A further 700 ml of hexane (in total 535 g=800 ml) were added and the reaction was again initiated with 5 ml of t-butyl chloride. Following a temperature rise (reaction kick-off) the internal temperature was adjusted to 50° C. and the pressure reduced until the solvent came to the boil (500 mbar). The remaining t-butyl chloride (total amount 92.6 g, 1 mol) was then added within 4 hours and the reaction continued for a further 1 hour. The vacuum was then released with argon, the reaction mixture cooled to room temperature and filtered, and washed with hexane.

693 g of a clear solution were obtained with a content of 0.96 mmol of t-butyl lithium per g of solution, which corresponds to a yield of 66.5%.

The reaction was performed in an analogous way at around 40° C. and under 400 mbar. 691 g of a clear solution were obtained with a content of 1.12 mmol of t-butyl lithium per g of solution, which corresponds to a yield of 77.4%.

The reaction was performed again in an analogous way at around 30° C. and under 300 mbar. 626 g of a clear solution were obtained with a content of 1.53 mmol of t-butyl lithium per g of solution, which corresponds to a yield of 95.8%.

These 3 examples show the direct synthesis of t-butyl lithium in hexane. The previously conventional circuitous route via synthesis in pentane with subsequent laborious solvent exchange can now be avoided with the process according to the invention. The increase in yield at lower temperatures can also clearly be seen.

EXAMPLE 3

Production of N-butyl Lithium in Methyl Cyclohexane at 50° C. under Vacuum 22.3 g of Li powder (3.2 mol) were stirred with 0.3 g of LiH powder in 100 ml of methyl cyclohexane for 30 minutes at room temperature and the reaction initiated by addition of 2 ml of n-butyl chloride.

A further 560 ml of hexane (in total 500 g=660 ml) were added and the reaction was again initiated with 2 ml of n-butyl chloride. Following a temperature rise the internal temperature was adjusted to 50° C. and the pressure reduced until the solvent came to the boil (190 mbar). 148.5 g (1.6 mol) of n-butyl chloride were then added within 120 minutes and the reaction continued for a further 30 minutes. The vacuum was then released with argon, the reaction mixture cooled to room temperature and filtered, and washed with methyl cyclohexane.

558 g of clear, colourless product solution were obtained with a content of 2.46 mmol/g of n-butyl lithium and 127 g of wash filtrate with a content of 0.76 mmol/g of n-butyl lithium. The isolated yield was 1.5 mol (91.8%)

EXAMPLE 4

Production of N-butyl Lithium in Toluene at 50° C. under Vacuum 22.3 g of Li powder (3.2 mol) were stirred with 0.3 g of LiH powder in 100 ml of toluene for 30 minutes at room temperature and the reaction initiated by addition of 2 ml of n-butyl chloride.

A further 485 ml of toluene (in total 500 g=585 ml) were added and again initiated with 2 ml of n-butyl chloride. Following a temperature rise the internal temperature was adjusted to 50° C. and the pressure reduced until the solvent came to the boil (140 mbar). 148.5 g (1.6 mol) of n-butyl chloride were then added within 120 minutes and the reaction continued for a further 30 minutes. The vacuum was then released with argon, the reaction mixture cooled to room temperature and filtered, and washed with toluene.

532 g of a clear, colourless product solution were obtained with a content of 2.45 mmol/g of n-butyl lithium and 133 g of wash filtrate with a content of 1.06 mmol/g of n-butyl lithium, which corresponds to a yield of 1.45 mol=90.3%.

What is claimed is:

1. A process for the production of an alkyl lithium compound comprising reacting metallic lithium with an alkyl halide in a solvent at reduced pressure and at the boiling point of the solvent.

2. The process according to claim 1, wherein the reaction is performed at a pressure of 10 to 900 mbar.

3. The process according to claim 2, wherein the reaction is performed at a pressure of 50 to 500 mbar.

4. The process according to claim 1, wherein the reaction is performed at a temperature of 0 to 80° C.

5. The process according to claim 2, wherein the reaction is performed at a temperature of 0 to 80° C.

6. The process according to claim 3, wherein the reaction is performed at a temperature of 0 to 80° C.

7. The process according to claim 4, wherein the temperature is from 20 to 50° C.

8. The process according to claim 5, wherein the temperature is from 20 to 50° C.

9. The process according to claim 6, wherein the temperature is from 20 to 50° C.

10. The process according to claim 1, wherein said solvent is an aliphatic or aromatic hydrocarbon.

11. The process according to claim 2, wherein said solvent is an aliphatic or aromatic hydrocarbon.

12. The process according to claim 3, wherein said solvent is an aliphatic or aromatic hydrocarbon.

13. The process according to claim 4, wherein said solvent is an aliphatic or aromatic hydrocarbon.

14. The process according to claim 5, wherein said solvent is an aliphatic or aromatic hydrocarbon.

15. The process according to claim 6, wherein said solvent is an aliphatic or aromatic hydrocarbon.

16. The process according to claim 7, wherein said solvent is an aliphatic or aromatic hydrocarbon.

17. The process according to claim 8, wherein said solvent is an aliphatic or aromatic hydrocarbon.

18. The process according to claim 9, wherein said solvent is an aliphatic or aromatic hydrocarbon.

19. The process according to claim 1, wherein said reduced pressure is below atmospheric pressure.

20. The process according to claim 19, wherein said reaction is conducted in a vessel.

21. The process according to claim 1, wherein said reaction is conducted in a vessel.

* * * * *